(12) United States Patent
Willenbring et al.

(10) Patent No.: US 6,790,412 B2
(45) Date of Patent: Sep. 14, 2004

(54) BULK VESSEL FEEDER

(75) Inventors: Armer J. Willenbring, Minnetonka, MN (US); Rodney E. Haning, Bloomington, MN (US); Jon P. Lindquist, Blaine, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 502 days.

(21) Appl. No.: 09/777,750

(22) Filed: Feb. 6, 2001

(65) Prior Publication Data

US 2002/0106305 A1 Aug. 8, 2002

(51) Int. Cl.[7] .............................. B32B 5/02; B65G 47/24
(52) U.S. Cl. ............................ 422/63; 422/65; 422/67; 198/392
(58) Field of Search ................... 422/63–65, 67; 198/392, 393

(56) References Cited

U.S. PATENT DOCUMENTS

| | | |
|---|---|---|
| 1,311,590 A | 7/1919 | Bingham |
| 1,653,480 A | 12/1927 | Soubier |
| 2,341,265 A | 2/1944 | Crawford |
| 2,734,627 A | 2/1956 | Shields |
| 2,936,059 A | 5/1960 | Hakogi |
| 2,954,862 A | 10/1960 | Clark |
| 2,987,180 A | 6/1961 | Shields |
| 3,119,487 A | 1/1964 | Wyle et al. |
| 3,221,857 A | 12/1965 | Keller |
| 3,276,566 A | 10/1966 | Raasch |
| 3,338,373 A | 8/1967 | Aldlin et al. |
| 3,372,310 A | 3/1968 | Kantor |
| 3,537,567 A | 11/1970 | Nowicki |
| 3,633,730 A | 1/1972 | Deutschbein |
| 4,244,459 A | 1/1981 | Garrett |
| 4,634,575 A | 1/1987 | Kawakami et al. |
| 4,681,230 A | 7/1987 | Küpper |
| 4,832,175 A | 5/1989 | MacIntyre |
| 4,944,382 A | 7/1990 | Gradoboev et al. |
| 5,065,852 A | 11/1991 | Marti |
| 5,143,506 A | 9/1992 | Sticht |
| 5,186,307 A | 2/1993 | Doudement et al. |
| 5,191,961 A * | 3/1993 | Wilson et al. ............ 198/392 |
| 5,314,072 A | 5/1994 | Frankel et al. |
| 5,439,093 A | 8/1995 | Drewitz |
| 5,443,149 A | 8/1995 | Rohwetter et al. |
| 5,582,796 A | 12/1996 | Carey et al. |
| 5,637,275 A * | 6/1997 | Carey et al. ............... 422/64 |
| 5,653,940 A * | 8/1997 | Carey et al. ............... 422/52 |
| 6,065,587 A * | 5/2000 | Schindel ................ 198/465.1 |
| 6,074,615 A * | 6/2000 | Lewis et al. .............. 422/102 |
| 6,362,272 B1 * | 3/2002 | Tadaki et al. ............. 524/555 |
| 6,436,349 B1 * | 8/2002 | Carey et al. ............... 422/64 |
| 6,443,291 B2 * | 9/2002 | Rivers, Jr. ................ 198/392 |
| 6,498,037 B1 * | 12/2002 | Carey et al. ............... 436/50 |
| 6,555,062 B1 * | 4/2003 | Lewis et al. ............... 422/63 |
| 6,599,476 B1 * | 7/2003 | Watson et al. ............. 422/63 |

* cited by examiner

Primary Examiner—Jill Warden
(74) Attorney, Agent, or Firm—Hogan & Hartson, LLP

(57) ABSTRACT

An apparatus for feeding to an automated analyzer a bulk quantity of vessels is provided. The bulk vessel feeding apparatus has a frame structure, a vessel hopper and an elevator chain supported by the frame structure. The elevator chain is driven by a drive sprocket and carries a plurality of scoopers for transporting the vessels from the hopper to a sorting and orienting mechanism. The sorting and orienting mechanism has two actuated rams for ejecting the vessels from the scoopers into a guide, while sorting and orienting the vessels, such that they are all headed by their closed ends when traveling in the guide. The guide leads to an escape mechanism for dispensing the vessels one at a time to the analyzer.

34 Claims, 7 Drawing Sheets

BULK VESSEL FEEDER

BACKGROUND OF THE INVENTION

1. Area of the Art

The invention relates generally to vessel handling mechanisms for automated chemical analyzers, and specifically to bulk vessel feeders for automated chemical analyzers.

2. Description of the Prior Art

Automated chemical analyzers are widely used in clinical chemistry sampling and analyzing applications, and are often involved in the supplying of bulk vessels for performing various assays. The basic functions of a mechanism for supplying bulk vessels often involve feeding and sorting the vessels for processing and analyzing by the automated chemical analyzers.

The following references are found to be pertinent to the field of the present invention:

U.S. Pat. No. 4,944,382, issued to Gradoboev et al on Jul. 31, 1990, disclosed an apparatus for orienting parts in feeding devices of various units. The apparatus includes a screw conveyor and members for picking up improperly oriented parts and means for reorienting parts.

U.S. Pat. No. 5,314,072, issued to Frankel et al. on May 24, 1994, disclosed a method of detecting whether bottles for recycling contain chlorine. The method includes the steps of sensing whether the bottles are clear and/or colored, and the step of irradiating the bottles with X-rays to detect the presence of chlorine. It further includes the step of emitting and passing circularly polarized light through the bottles for determining the composition of the bottles.

U.S. Pat. No. 5,439,093, issued to Drewitz on Aug. 8, 1995, disclosed an apparatus for unscrambling a population of containers. The apparatus includes a plurality of container handling stations between an in-feed station or guide and an output station, each having two container engaging members and a rotating means for rotating the container engaging members to alter the orientation of the containers.

U.S. Pat. No. 4,634,575, issued to Kawakami et al. on Jan. 6, 1987, disclosed an automatic cuvette loading apparatus for supplying cuvettes contained in magazines one by one into successive recesses of a cuvette holding turntable. The apparatus includes a plurality of magazines and means for feeding the magazines into a cuvette loading position.

U.S. Pat. No. 4,832,175, issued to MacIntyre on May 23, 1989, disclosed a sorting and orienting structure. The structure includes an annular sorting and orienting table and a drive shaft for rotating the table to sort and orient work pieces.

U.S. Pat. No. 5,065,852, issued to Marti on Nov. 19, 1991, disclosed a machine for automatically positioning and feeding bottles. The machine includes two hoppers (a main hopper and a receiving hopper), a container holder support means supported below the main hopper, and means for driving the container holder support means along a path adjacent to a peripheral portion of the bottom of the main hopper.

U.S. Pat. No. 5,143,506, issued to Sticht on Sep. 1, 1992, disclosed an apparatus for aligning and sorting disordered parts. The apparatus includes two conveyors, including an elevator conveyor and a linear sorting conveyor.

U.S. Pat. No. 5,186,307, issued to Doudement et al. on Feb. 16, 1993, disclosed a transport device for removing interlocked preforms used in manufacturing synthetic bottles. The device includes a conveyor track incorporating two substantial parallel slide-rails.

U.S. Pat. No. 5,443,149, issued to Rohwetter et al on Aug. 22, 1995, disclosed an apparatus for aligning parts supplied in a disordered fashion. The apparatus includes a rotatable drum having a bottom made of at least two substantially coaxial discs arranged one above the other.

U.S. Pat. No. 5,582,796, issued to Glen A. Carey et al. on Dec. 10, 1996, disclosed a feed and orientation mechanism in an automated analyzer. The mechanism includes an orientation chute as a means for orienting a cuvette. The orientation chute has a pair of upper parallel slide surfaces which are separated by a slot which has a longitudinal sliding axis for receiving the cuvette from the conveyor belt at the first point so that the flanges of the cuvette are parallel with the longitudinal axis of the slot and are supported on said slide surfaces. The cuvette extends downwardly in the slot to enable the cuvette to slide downwardly on the chute along the axis from the first point to the second point.

Other references also found to be of interest to the field of the present invention include: U.S. Pat. No. 1,311,590 issued to Bingham on Jul. 29, 1919; U.S. Pat. No. 1,653,480 issued to Soubier on Dec. 20, 1927; U.S. Pat. No. 2,341,265 issued to Crawford on Feb. 8, 1944; U.S. Pat. No. 2,734,627 issued to Shields on Feb. 14, 1956; U.S. Pat. No. 2,936,059 issued to Hakogi on May 10, 1960; U.S. Pat. No. 2,954,862 issued to Clark on Oct. 4, 1960; U.S. Pat. No. 2,987,180 issued to Shields on Jun. 6, 1961; U.S. Pat. No. 3,119,487 issued to Wyle et al. on Jan. 28, 1964; U.S. Pat. No. 3,221,857 issued to Keller on Dec. 7, 1965; U.S. Pat. No. 3,276,566 issued to Raasch on Oct. 4, 1966; U.S. Pat. No. 3,338,373 issued to Aidlin et al. on Aug. 29, 1967; U.S. Pat. No. 3,372,310 issued to Kantor on Mar. 5, 1968; U.S. Pat. No. 3,537,567 issued to Nowicki on Nov. 3, 1970; U.S. Pat. No. 3,633,730 issued to Deutschbein on Jan. 11, 1972; U.S. Pat. No. 4,244,459 issued to Garrett on Jan. 13, 1981; and U.S. Pat. No. 4,681,230 issued to Kupper on Jul. 21, 1987. These references are generally related to the field of container handling technology.

While many cited references have disclosed mechanisms for handling bulk vessels, they all have certain limitations and therefore cannot satisfy the needs addressed by the present invention. For example, some prior mechanisms are designed to handle rectangular shaped cuvettes with planar flanges but not circular shaped vessels. In addition, many prior mechanisms utilize an inclined sliding chute for sorting the vessels. Furthermore, many prior mechanisms are not designed to feed vessels to a carriage module that moves randomly.

Bulk vessels are preferred in many automated chemical analyzers because bulk vessels are less costly than vessels with packaging for a vessel handler. Bulk vessels can also be stored economically and require minimal instrument space for vessel storage and vessel feeding apparatus. In addition, handling bulk vessels requires minimum operator training and reduces the problems caused by human errors.

Therefore, it is desirable to provide a new system for feeding and sorting bulk vessels for an automated chemical analyzer.

SUMMARY OF THE INVENTION

It is an object of the present invention to provide a system for sorting and feeding bulk vessels to an automated chemical analyzer.

The objects and advantages of the present invention are achieved in a bulk vessel feeder of the present invention by having a sorting and orienting mechanism, intercepting the vessels and ejecting them into a guide, while sorting and orienting the vessels such that they are all headed by their closed ends when traveling in the guide.

In accordance with embodiments of the present invention, the bulk vessel feeder has a frame structure with two upright side plates connected in a spaced-apart parallel relationship. An elevator chain driven by a drive sprocket is supported between the two side plates and carries a series of scoopers. Each scooper is configured to carry at least one vessel in a horizontal orientation. The bulk vessel feeder has a sorting and orienting mechanism mounted on the frame structure at a location intercepting the vessels carried by the scoopers. The sorting and orienting mechanism includes a first ram for engaging the closed end of the vessels carried by the scoopers, if the closed ends of the vessels are facing the first ram, and ejecting such vessels one at a time from the scoopers into a first passage way with their open end headed into the first passage way first. The sorting and orienting mechanism also has a second ram for engaging the open end of the vessels carried by the scoopers, if the open ends of the vessels are facing the second ram, and ejecting such vessels one at a time from the scoopers into the second passageway with their closed end headed into the second passageway first. Both passageways feed into a guide that leads to an escape mechanism, which dispenses the vessels one at a time to an automated chemical analyzer.

Such an arrangement has been found to provide a number of advantages. As explained in greater detail below, it has been found that the bulk vessel feeder of the present invention provides the features of feeding and sorting of circular shaped vessel to a carriage module that makes random moves. It also utilizes open-and-closed end features for sorting vessels, which is more robust than solely relying on gravity force because the vessels have minimal mass.

Another important feature of the bulk vessel feeder of the present invention is that it utilizes a controllable actuator to forcibly move the vessels during orientation, which reduces the susceptibility of vessel jamming due to electrostatic charge buildup on the vessels. In addition, the bulk vessel feeder of the present invention employs large scoopers for sweeping a large horizontal-plan area in the hopper in conjunction with the staging section in the hopper that pre-orients the vessels to produce a high yield of proper oriented vessels in the scoopers. Furthermore, the angling of the track of the bulk vessel feeder of the present invention permits the excess vessels to be dispensed back into the hopper in a preferred orientation. Similarly, the reciprocating escapement of the vessel feeder delivers vessels on demand to the shuttle module. Overall, the bulk vessel feeder of the present invention has a very compact design which delivers vessels at a high throughput and can be adapted to a variety of vessel shapes.

The bulk vessel feeder of the present invention is well suited for use in conjunction with an automated chemical analyzer, such as, but not limited to, Access Nexgen (Beckman Coulter Inc., CA).

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

The present invention is directed to a new bulk vessel feeder used in conjunction with an automated chemical analyzer. The bulk vessel feeder is designed to feed bulk quantity of test-tube-like reaction vessels or other cylindrical-shaped objects.

Figure 1:
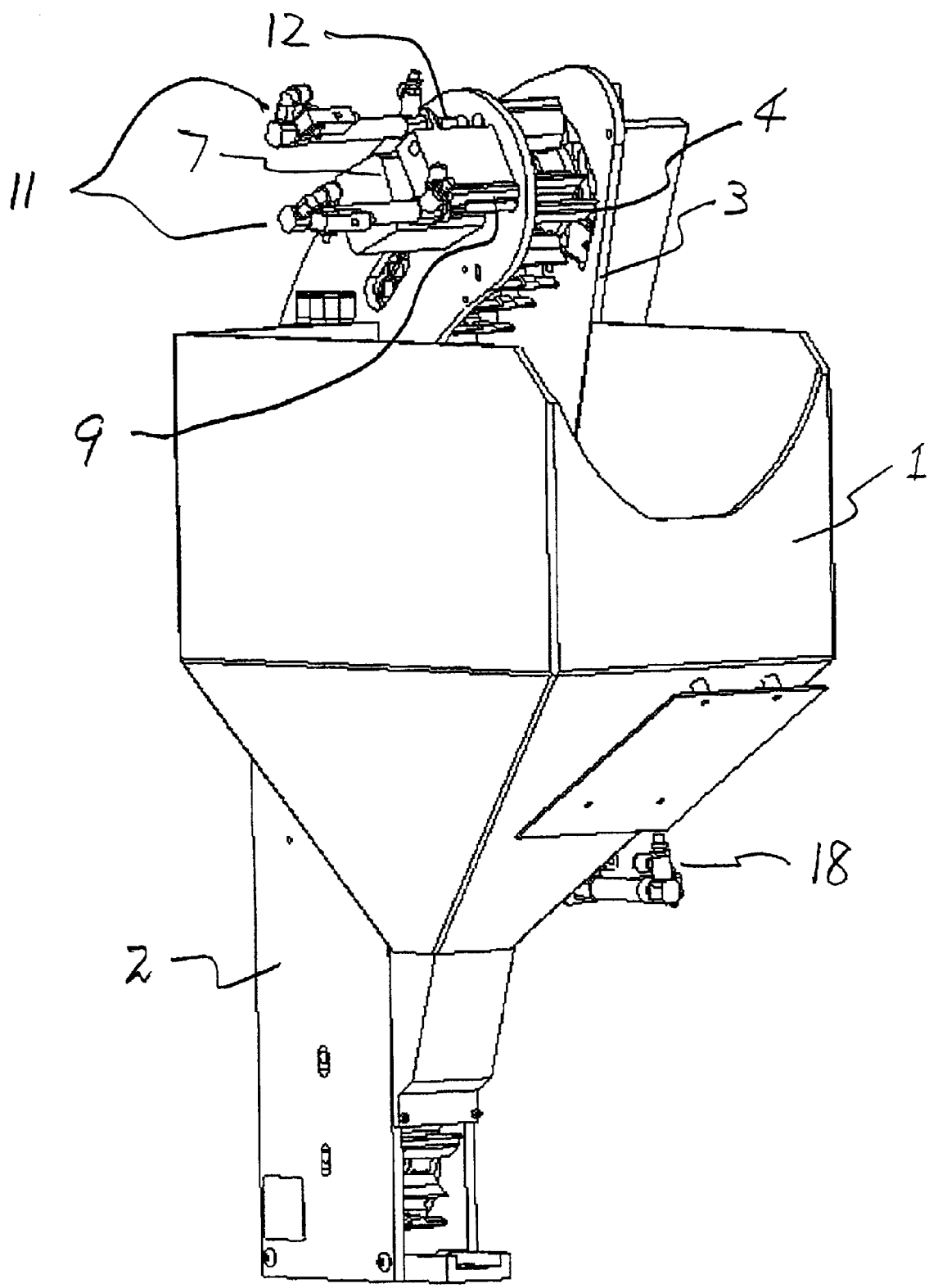
FIG. 1 is a perspective view of a preferred embodiment of the bulk vessel feeder of the present invention.
Figure 2:
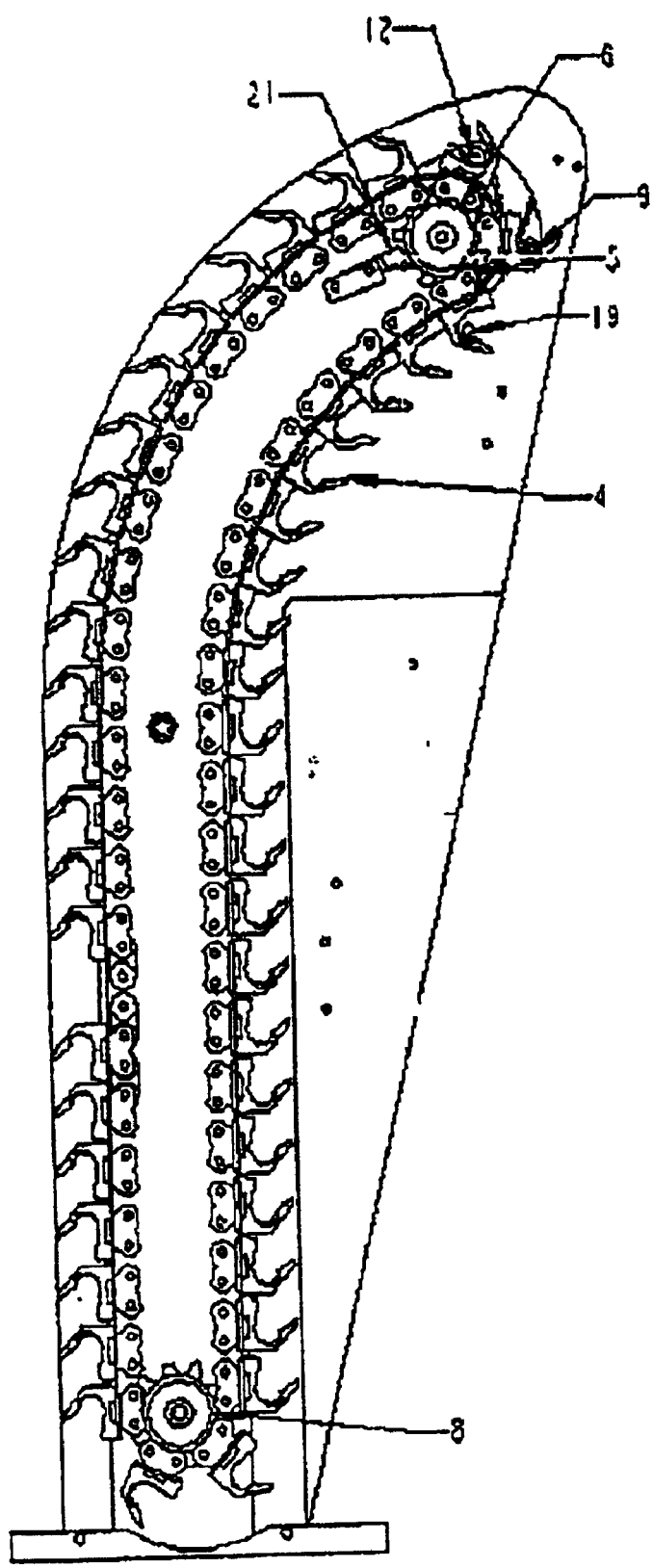
FIG. 2 is an exposed side elevation view of the bulk vessel feeder of the present invention, showing the vertical elevator chain with vessel scoopers.
Figure 3:
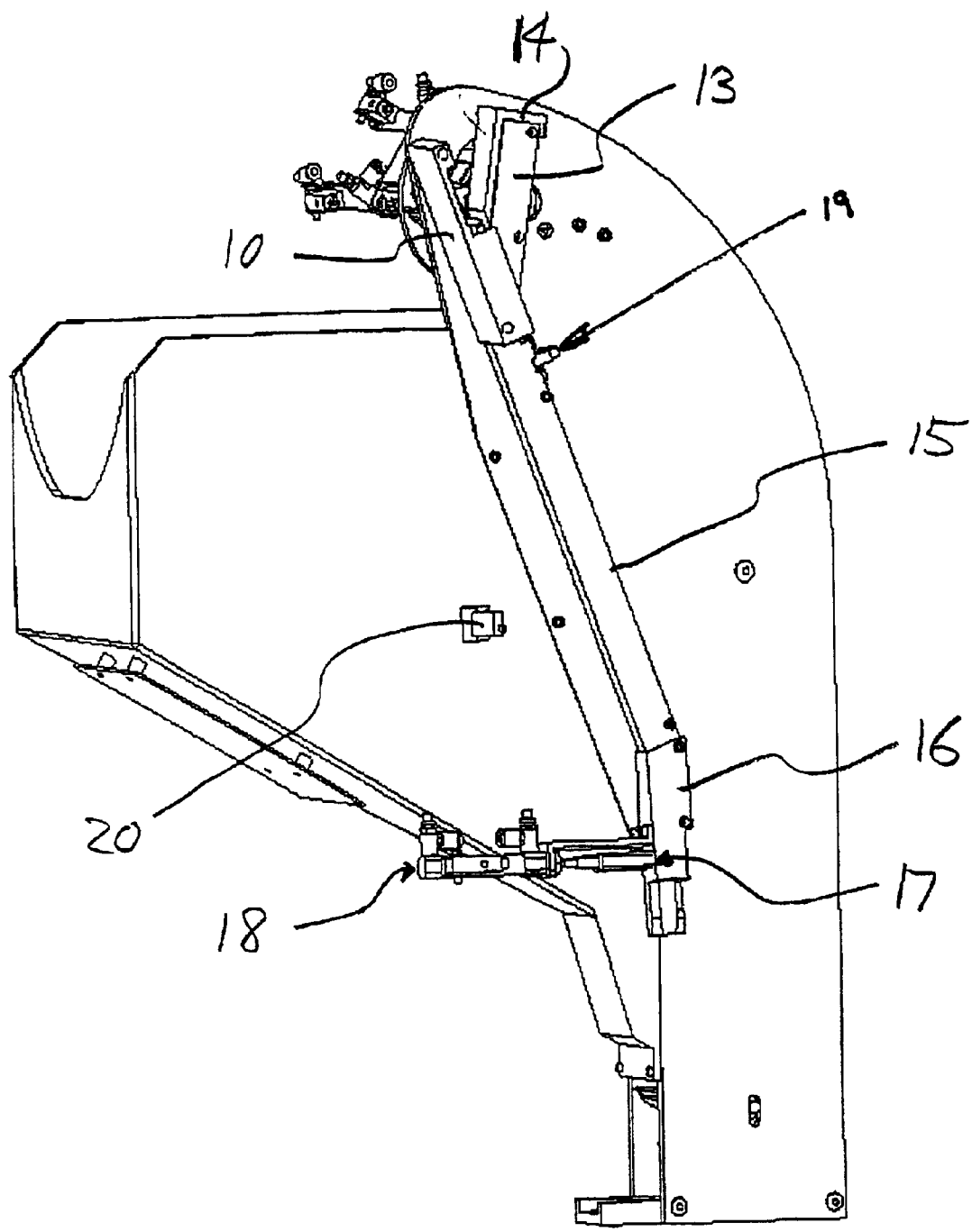
FIG. 3 is another side elevation view of the bulk vessel feeder of the present invention, showing the escapement mechanism.

Referring to FIGS. 1 through 3, the bulk vessel feeder of the present invention comprises the following main components: a vessel hopper 1, a left side plate 2, a right side plate 3, vessel scoopers 4, an elevator chain 5, a drive sprocket 6, a drive motor 7, an idler sprocket 8, a first ram 9, a first passageway 10, ram actuators 11, a second ram 12, a second passageway 13, a cover 14, an escrow guide 15, an escapement housing 16, an escapement 17, an escapement actuator 18, a vessel sensor 19, hopper sensors 20, and a sprocket sensor 21.

The structural and functional features of the above-mentioned components of the bulk vessel feeder of the present invention will become apparent from the following description.

The bulk vessel feeder of the present invention has a frame structure primarily formed by the left side plate 2 and the right side plate 3. The vessel hopper 1 is mounted to the frame structure or position adjacent to the frame structure, and is a large container for receiving a bulk quantity of reaction vessels. In accordance with one embodiment of the present invention, the vessel hopper 1 has an inclined bottom surface to feed the vessels to a staging area at the bottom of the hopper 1. The staging area of the bottom of the hopper 1 may be, as an example, approximately 4 inches high. The staging area orients the vessels to maximize the probability that a vessel will fall into the nest at the bottom of the valley between the front-top and the vertical surfaces of the scoopers 4. Below the staging area of the hopper 1 is a gate area which prevents vessels from falling out of the device by going between the scoopers 4 and the hopper 1.

The bulk vessel feeder of the present invention also has a transport mechanism supported by the frame structure. The transport mechanism includes the vessel scoopers 4, the elevator chain 5, the drive sprocket 6, the drive motor 7 and the idle sprocket 8. The scoopers 4 are attached to an elevator chain 5. The elevator chain 5 is driven by a drive sprocket 6, mounted between the lift side plate 2 and the right side plate 3. The drive sprocket 6 is in turn driven by a drive motor 7, mounted on the left side plate 2.

Each scooper 4 has flanges on each side for guiding it in a specified path by having the flanges riding in respective grooves in the left side plate 2 and the right side plate 3. The elevator chain 5 and scoopers 4 form an endless loop, which may be, as an example, approximately 48 inches long. An idler sprocket 8 is mounted between the left side plate 2 and the right side plate 3 at the bottom of the elevator chain 5 to help guide the elevator chain 5 and scoopers 4.

The vessel scoopers 4 lift the vessels out of the hopper 1 and stir vessels contained in the hopper 1. The scoopers 4 are designed with a large holding area to maximize the chance for the scoopers 4 to capture at least one vessel in the nest of each scooper. The extra vessels in a scooper can easily be discarded back into the hopper 1.

The shape of the scoopers and their orientation in the elevator chain 5 are designed in a way, such that, as the scoopers 4 approach the drive sprocket 6, excess vessels will slide off of the scoopers 4 and fall back into the hopper 1, leaving only one vessel in the nest of each scooper 4. Most of the vessels that fall off of the scoopers 4 and return to the hopper 1 are parallel to each other and generally parallel to the scoopers 4, thus enhancing their entry into the vessel staging area of hopper 1.

The bulk vessel feeder of the present invention has a mechanism for sorting and orienting the bulk vessels. The sorting and orienting mechanism includes the two rams 9 and 12, the two corresponding passageways 10 and 13, the ram actuators 11, the cover 14, and the escrow guide 15.

Vessels in the nest of the scoopers 4 may have their open end either facing left to the left side plate 2 or facing right to the right side plate 3. The two rams 9 and 12 are mounted at spaced-apart locations near the top of the elevator chain 5 and adjacent to the sprocket 6. The two rams 9 and 12 are actuated by actuators 11 mounted on the left side plate 2. The first ram 9 has a dimension smaller than the inside diameter of the vessels, but the second ram 12 has a dimension larger than the inside diameter of the vessels. Two passageways 10 and 13 are mounted on the right side plate 3 at locations corresponding to the locations of the two rams 9 and 12, respectively.

Figure 7:
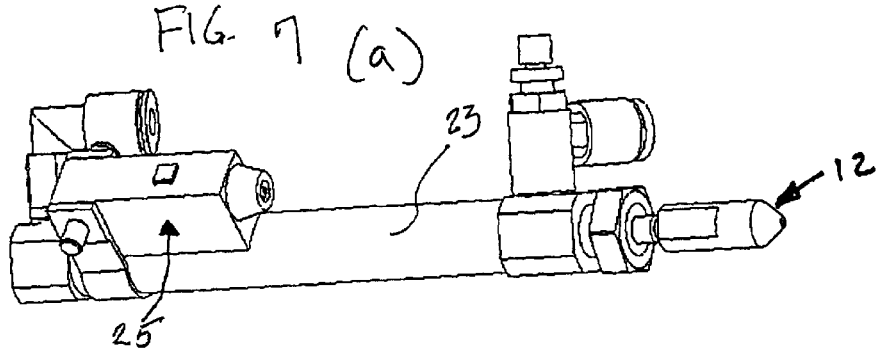
FIGS. 7(a) and (b) are enlarged perspective view of the first and second rams of the bulk vessel feeder of the present invention.
Figure 7:
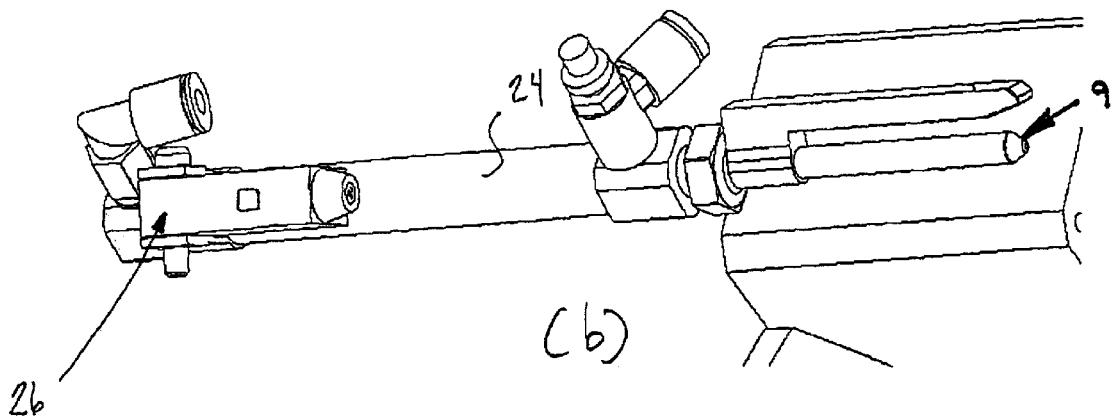

Referring to FIGS. 7(*a*) and (*b*), there are shown the configurations the second ram 12 and first ram 9, respectively. The first ram 9 has a generally "U" shaped configuration with its legs and open end facing the vessel. Moving magnets are located inside the cylinders 23 and 24 connected to the rams 12 and 9 respectively, and hall sensors 25 and 26 are mounted outside of these cylinders 23 and 24 respectively. The generally cylindrical shaped lower leg of ram 9 enters the vessel if the open end of the vessel faces the ram 9. The generally rectangular shaped upper leg of ram 9 goes above the vessel if the vessel's open end faces the ram 9. The upper leg ensures that the vessel moves correctly into the guide apparatus even if the vessel bounces upward during its movement into the guide apparatus.

Figure 4:
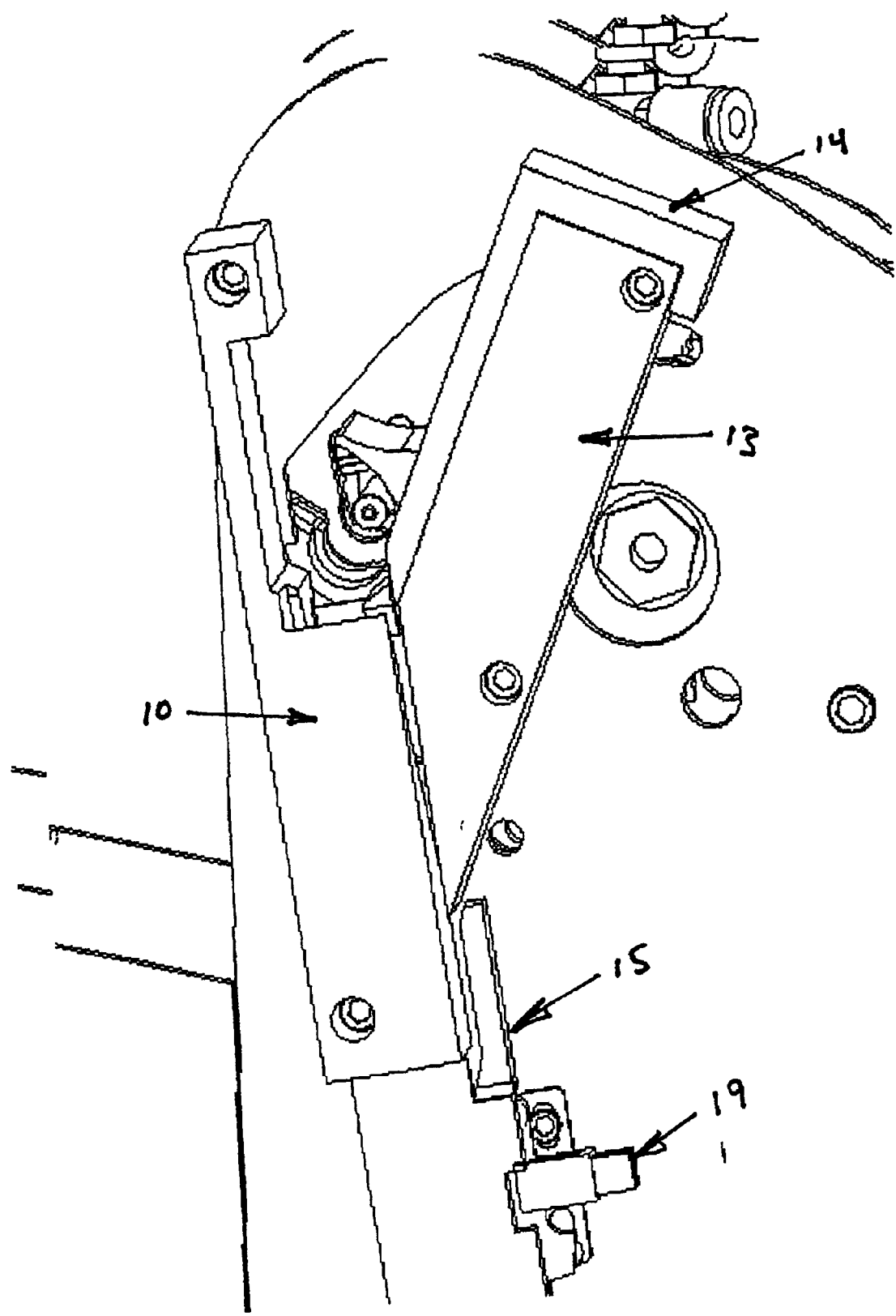
FIG. 4 is an enlarged perspective view of part of the sorting and orienting mechanism of the bulk vessel feeder of the present invention.
Figure 5:
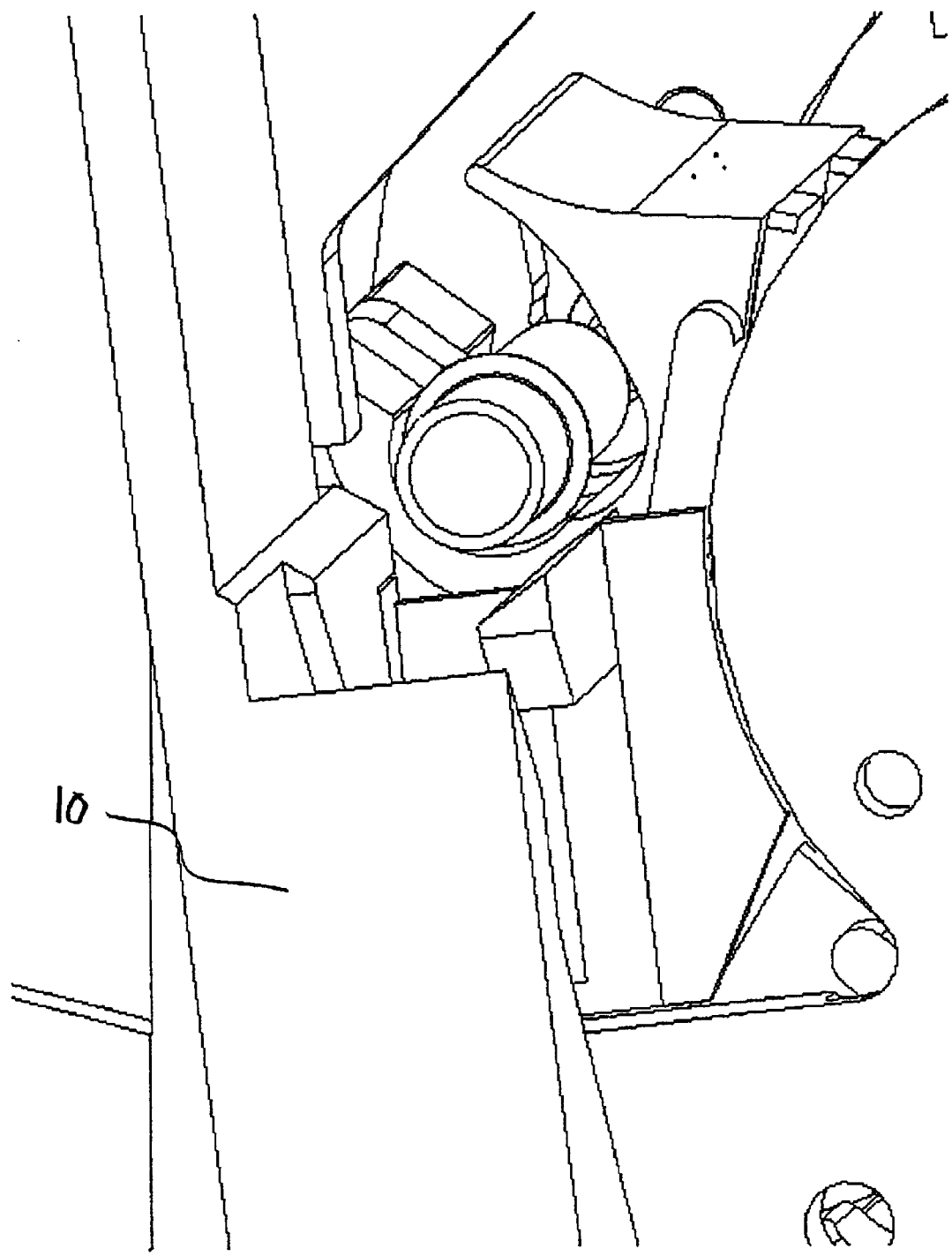
FIG. 5 is an enlarged perspective view of part of the sorting and orienting mechanism of the bulk vessel feeder of the present invention, showing a vessel ejected by the first ram to and over a slot opening of a guide leading to escapement.
Figure 6:
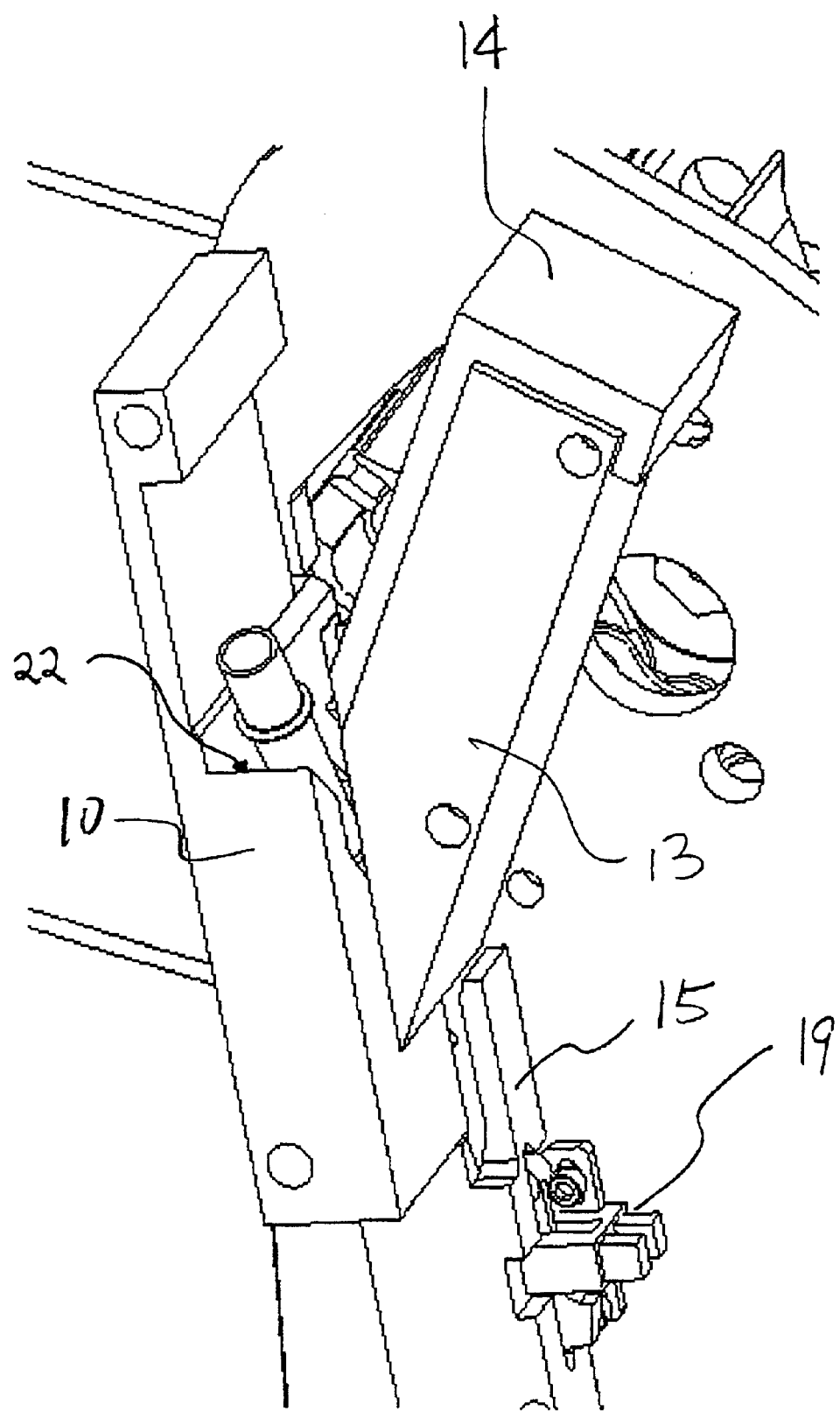
FIG. 6 is an enlarged perspective view of part of the sorting and orienting mechanism of the bulk vessel feeder of the present invention, showing the reaction vessel falls down the guide in correct orientation.

Referring to FIGS. 4 through 6 in conjunction with FIGS. 1 through 3, when a vessel is carried by a scooper 4 and reaches the location of first ram 9, one of the actuators 11 will actuate the first ram 9 to move from left to right. If the closed end of the vessel faces to the left (and thus faces the first ram 9) and the open end of the vessel faces to the right, then the first ram 9 will push the vessel to the right. FIG. 5 shows a vessel before it enters the lower guide and shows elements of the lower guide. FIG. 6 shows a vessel after it hits the first step 22 and is about to enter the escrow guide.

The passageway 10 has an orientation mechanism to ensure that the closed end of the vessel exits the passageway 10 first. The orientation mechanism includes a slot at the opening of the passageway 10. The width of the slot is narrower than the outside diameter of the ring of the vessel, except at the right where the slot ends. As the vessel with the open end facing right is pushed over the slot, its open end is prevented from falling into the passageway 10 because the width of the slot is narrower than the outside diameter of the ring of the vessel. As the ring of the vessel reaches the end of the slot, the open end of the vessel will ride on the front step of the slot and the closed end of the vessel will still be riding on the scooper, such that the vessel is still prevented from falling into the passageway 10.

At the end of the stroke of the first ram 9, the closed end of the vessel will be pushed off the scooper, falling into the slot first due to gravity, while the open end of the vessel is still riding on the front step of the slot. Finally, as the closed end of the vessel falls into the passageway 10 and therefore tilts the vessel, the open end of the vessel slides off the front step of the slot, and the whole vessel falls into the passageway 10 as the widened end of the slot allows the ring of the vessel to pass through. At faster speeds, the vessel hitting the inclined ramp at the first step forces the open end upward rotating the vessel end for end helping to move the closed end into the slot. This mechanism ensures that the closed end of the vessel will drop into the passageway 10 first as it leads to the escrow guide 15.

If the open end of the vessel faces to the left, then the lower leg of the first ram 9 will enter the open end of the vessel and the vessel will not be pushed out but rather remain in place, since the first ram 9 simply extends inside the vessel. As the first ram 9 is retracted, the left sidewall 2 will prevent the vessel from moving to the left, so the vessel stays in and moves with the scooper 4 as the scooper 4 advances to the location where the second ram 12 is located.

When the vessel with its open end facing left is carried by the scooper 4 and reaches the location of the second ram 12, the other one of the actuators 11 will actuate the second ram 12 to move from left to right. Since the second ram 12 is large enough to engage the open end of the vessel, it pushes the vessel into the second passageway 13, which also leads to the escrow guide 15, where the closed end of the vessel is directed downward in the passageway 13.

Since the only vessels remaining in the scooper 4 where the second ram 12 is located are those with their open ends facing to the left, all vessels at this location are ejected. Thus, no matter which direction the vessels are facing initially in the scoopers, they end up in the escrow guide 15 with their open ends upward and closed end downward.

The escrow guide 15 leads the vessels with their open ends upward and closed end downward to an escapement mechanism of the bulk vessel feeder of the present invention, which includes the escapement housing 16, the escapement 17 and the escapement actuator 18. The escapement 17 dispenses vessels one at a time when the escapement actuator 18 is extended. The escapement actuator 18 is then retracted, permitting the next vessel to be ready for escapement when the escapement actuator 18 is extended.

The bulk vessel feeder of the present invention further has an instrument control device for control and coordinates the movement of the transporting mechanism, the sorting and orienting mechanism, and the escapement mechanism. The instrument control device is electrically coupled to various sensors, including the vessel sensor 19, the hopper sensors 20, and the sprocket sensor 21.

The vessel sensor 19 is mounted near the top of the escrow guide 15 on the right side plate 3. It is intermittently blocked as vessels enter the guide 15 and continuously blocked when vessels are at or above the sensor in the guide. The instrument control system uses this sensor 19 together with the number of dispensed vessels from the escapement housing 16 to maintain the level of vessels in the escrow guide 15 by advancing the drive motor 7 and rams 9 and 12 as required.

The pair of hopper sensors 20 is mounted on the opposite sides of the vessel hopper 1, respectively. The hopper sensors 20 monitor whether there are sufficient vessels in the hopper for the quantity of tests to be run. When the path between the emitter and detector pair of hopper sensors 20 becomes unblocked, the instrument control system starts counting down from a predetermined number as vessels are removed from the hopper 1. At a second predetermined number of vessels in the hopper 1, the operator is warned that the hopper 1 needs to be filled. When the number of vessels available reaches a near empty count, new tests are halted because there are insufficient vessels to process additional tests. The stirring action of the scoopers 4 causes the top surface of the vessels in the hopper 1 to have a characteristic profile at the sensor level permitting the quantity of vessels to be predictable when the sensor path is broken.

The sprocket sensor 21 is mounted near the drive sprocket 6 for detecting and signaling the correct sprocket stopping position. This location reduces the effect of chain stretch (wear) on the scooper stopping position.

The bulk vessel feeder of the present invention has many unique and advantageous features, including sorting of vessels using open-and-closed end features, orienting vessels using specialized guide paths, picking up one vessel at a time using the scoop-and-dump method, dispensing shouldered vessels using a reciprocating escapement. All these features are integrated into a compact and effective system.

The bulk vessel feeder of the present invention can be used to accomplish a variety of tasks. For example, it may be used to feed test-tube-like vessels. It may also be used to feed cylindrical-shaped objects with a single ejector and with or without the escapement. Of course, it is to be understood that the bulk vessel feeder of the present invention may be modified to accommodate different shaped reaction vessels. Such modifications can be made without undue experimentation by one skilled in the art in view of the teaching of the present invention.

The foregoing is meant to illustrate, but not to limit, the scope of the invention. Indeed, those of ordinary skill in the art can readily envision and produce further embodiments, based on the teachings herein, without undue experimentation. Suitable materials are commercially available and would be known to those of ordinary skill in the art in view of this disclosure.

It is to be understood that the form of the device depicted in the figures has been chosen only for the purpose of describing a particular embodiment and function of the invention, and that the material of the invention can be addressed in various ways and incorporated in other types of devices, all of which will be evident to those working in the art.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An apparatus for feeding to an automated analyzer a bulk quantity of vessels, each having an elongated body with a first end and a second end, comprising:

a. a frame structure;

b. means supported by said frame structure for transporting said vessels along a path;

c. a sorting and orienting mechanism, mounted on said frame structure at a location adjacent to said path and intercepting said vessels transported, for ejecting said sorted vessels from said transporting means into a guide, and orienting said vessels, such that they are all headed by their first ends when exiting said guide, wherein said sorting and orienting mechanism comprises a first ram for engaging said first end of said vessels transported if said first ends of said vessels are facing said first ram, and ejecting such vessels one at a time from said transporting means into said guide;

d. an escape mechanism mounted to said frame and connected to said guide for receiving said sorted and oriented vessels and dispensing them one at a time; and e. means for controlling and coordinating the movement of said transporting means, said sorting and orienting mechanism, and said escape mechanism.

2. The apparatus as defined in claim 1, wherein said frame structure comprises two upright side plates connected in a spaced-apart parallel relationship for supporting said transporting means.

3. The apparatus as defined in claim 1, further comprising a vessel hopper attached to said frame structure for receiving said bulk quantity of vessels and supplying them to said transporting means.

4. The apparatus as defined in claim 1, wherein said transporting means comprises an elevator chain moveable along said path for transporting said vessels to said location of said sorting and orienting mechanism.

5. The apparatus as defined in claim 4, wherein said transporting means further comprises a drive sprocket for driving said elevator chain to move along said path.

6. The apparatus as defined in claim 5, wherein said transporting means further comprises a drive motor for driving said drive sprocket.

7. The apparatus as defined in claim 5, wherein said transporting means further comprises an idle sprocket engaged with said elevator chain.

8. The apparatus as defined in claim 4, wherein said transporting means further comprises a multiplicity of scoopers carried by said elevator chain.

9. The apparatus as defined in claim 8, wherein each scooper is configured to transport said vessels in a horizontal orientation.

10. The apparatus as defined in claim 1, further comprising means for maneuvering said vessels ejected by said first ram, such that their first ends enter said guide first.

11. The apparatus as defined in claim 1, wherein said sorting and orienting mechanism further comprises a second ram for engaging said second end of said vessels transported if said second ends of said vessels are facing said second ram, and ejecting such vessels one at a time from said transporting means into said guide with said first ends of such vessels enter said guide first.

12. The apparatus as defined in claim 11, wherein said sorting and orienting mechanism further comprises ram actuators for actuating said first and second rams, respectively.

13. The apparatus as defined in claim 1, wherein said escaping mechanism comprises an escapement actuator.

14. The apparatus as defined in claim 8, further comprising a second ram for engaging said second end of said vessels transported if said second ends of said vessels are facing said second ram and a vessel sensor mounted on said frame structure and electrically coupled to said controlling and coordinating means for controlling the movement of the scoopers and the first and the second rams.

15. The apparatus as defined in claim 3, further comprising a hopper sensor mounted on said vessel hopper and electrically coupled to said controlling and coordinating means for detecting the amount of vessels remaining in said hopper.

16. The apparatus as defined in claim 3, further comprising a sprocket sensor mounted on said frame structure adjacent to said drive sprocket and electrically coupled to said controlling and coordinating means for detecting the correct stopping position of said drive sprocket.

17. An apparatus for feeding to an automated analyzer a bulk quantity of vessels each having an elongated body with a first end and a second end, comprising:
   a. a frame structure having two upright side plates connected in a spaced-apart parallel relationship;
   b. means supported by said frame structure for transporting said vessels along a path, including an elevator chain driven by a drive sprocket, and a multiplicity of scoopers carried by said elevator chain and each configured to transport said vessels in an horizontal orientation;
   c. a vessel hopper attached to said frame structure for receiving said bulk quantity of vessels and supplying them to said scoopers carried by said elevator chain;
   d. a sorting and orienting mechanism, mounted on said frame structure at a location adjacent to said path and intercepting said vessels carried by said scoopers;
   e. said sorting and orienting mechanism, including a first ram for engaging said first end of said vessels carried by said scoopers if said first ends of said vessels are facing said first ram, and ejecting such vessels one at a time from said scoopers into a guide;
   f. said sorting and orienting mechanism further including a second ram for engaging said second end of said vessels carried by said scoopers if said second ends of said vessels are facing said second ram, and ejecting such vessels one at a time from said scoopers into said guide;
   g. an escape mechanism mounted to said frame and connected to said guide for receiving said sorted and oriented vessels and dispensing them one at a time; and
   h. means for controlling and coordinating the movement of said transporting means, said sorting and orienting mechanism, and said escape mechanism.

18. The apparatus as defined in claim 17, wherein said transporting means further comprises a drive motor for driving said drive sprocket.

19. The apparatus as defined in claim 17, wherein said transporting means further comprises an idle sprocket engaged with said elevator chain.

20. The apparatus as defined in claim 17, wherein said sorting and orienting mechanism further comprises mean for maneuvering said vessels ejected by said first ram such that their first ends enter said guide first.

21. The apparatus as defined in claim 17, wherein said second ram ejects said such vessels, which have their second ends facing said second ram, from said scoopers into said guide with said first ends of such vessels enter said guide first.

22. The apparatus as defined in claim 17, wherein said sorting and orienting mechanism further comprises ram actuators for actuating said first and second rams, respectively.

23. The apparatus as defined in claim 17, wherein said escaping mechanism comprises an escapement actuator.

24. The apparatus as defined in claim 17, further comprising a vessel sensor mounted on said frame structure and electrically coupled to said controlling and coordinating means for controlling the movement of the scoopers and rams.

25. The apparatus as defined in claim 17, further comprising a hopper sensor mounted on said vessel hopper and electrically coupled to said controlling and coordinating means for detecting the amount of vessels remaining in said hopper.

26. The apparatus as defined in claim 17 further comprising a sprocket sensor mounted on said frame structure adjacent to said drive sprocket and electrically coupled to said controlling and coordinating means for detecting the correct stopping position of said drive sprocket.

27. An apparatus for feeding to an automated analyzer a bulk quantity of vessels, each having an elongated body with a first end and a second end, comprising:
   a. a frame structure having two upright side plates connected in a spaced-apart parallel relationship;
   b. means supported by said frame structure for transporting said vessels along a path, including an elevator chain driven by a drive sprocket, and a multiplicity of scoopers carried by said elevator chain and each configured to transport said vessels in an horizontal orientation;
   c. a vessel hopper attached to said frame structure for receiving said bulk quantity of vessels and supplying them to said scoopers carried by said elevator chain;
   d. a sorting and orienting mechanism, mounted on said frame structure at a location adjacent to said path and intercepting said vessels carried by said scoopers;
   e. said sorting and orienting mechanism, including a first ram for engaging said first end of said vessels carried by said scoopers, if said first ends of said vessels are facing said first ram, and ejecting such vessels one at a time from said scoopers into a guide, and also including mean for maneuvering said vessels ejected by said first ram, such that their first ends enter said guide first;
   f. said sorting and orienting mechanism further including a second ram for engaging said second end of said vessels transported if said second ends of said vessels are facing said second ram, and ejecting such vessels one at a time from said transporting means into said guide with said first ends of such vessels enter said guide first;
   g. an escape mechanism mounted to said frame and connected to said guide for receiving said sorted and oriented vessels and dispensing them one at a time; and
   h. means for controlling and coordinating the movement of said transporting means, said sorting and orienting mechanism, and said escape mechanism.

28. The apparatus as defined in claim 27, wherein said transporting means further comprises a drive motor for driving said drive sprocket.

29. The apparatus as defined in claim 27, wherein said transporting means further comprises an idle sprocket engaged with said elevator chain.

30. The apparatus as defined in claim 27, wherein said sorting and orienting mechanism further comprises ram actuators for actuating said first and second rams, respectively.

31. The apparatus as defined in claim 27, wherein said escaping mechanism comprises an escapement actuator.

32. The apparatus as defined in claim 27, further comprising a vessel sensor mounted on said frame structure and electrically coupled to said controlling and coordinating means for controlling the movement of the scoopers and rams.

33. The apparatus as defined in claim 27, further comprising a hopper sensor mounted on said vessel hopper and electrically coupled to said controlling and coordinating means for detecting the amount of vessels remaining in said hopper.

34. The apparatus as defined in claim 27, further comprising a sprocket sensor mounted on said frame structure adjacent to said drive sprocket and electrically coupled to said controlling and coordinating means for detecting the correct stopping position of said drive sprocket.

* * * * *